United States Patent
Furneaux et al.

(10) Patent No.: US 6,620,921 B1
(45) Date of Patent: Sep. 16, 2003

(54) GLUCOFURANOSES

(75) Inventors: Richard Hubert Furneaux, Wellington (NZ); Phillip Martin Rendle, Lower Hutt (NZ); Ian Michael Sims, Lower Hutt (NZ)

(73) Assignee: Industrial Research Limited, Auckland (NZ)

( * ) Notice: Subject to any disclaimer, the term of this patent is extended or adjusted under 35 U.S.C. 154(b) by 0 days.

(21) Appl. No.: 10/130,590

(22) PCT Filed: Nov. 16, 2000

(86) PCT No.: PCT/NZ00/00228

§ 371 (c)(1),
(2), (4) Date: Sep. 19, 2002

(87) PCT Pub. No.: WO01/36435

PCT Pub. Date: May 25, 2001

(30) Foreign Application Priority Data

Nov. 16, 1999 (NZ) ................................................ 501113

(51) Int. Cl.$^7$ ......................... C07H 13/04; C07H 13/02
(52) U.S. Cl. ......................... 536/4.1; 536/115; 536/119; 536/18.5; 536/18.6; 536/124; 536/17.1
(58) Field of Search ........................... 536/4.1, 115, 119, 536/17.1, 18.5, 18.6, 124

(56) References Cited

PUBLICATIONS

Dictionary of Organic Compounds 5th ed.,; Chapman & Hall: New York, vol. 3, 1982.

Funeaux, et al., "The influence of boric acid on the acetylation of aldoses: 'one–pot' syntheses of penta–O–acetyβ–D–glucofuranose and its crystalline propanoyl analogue", Perkin Trans. 1, 13, p 2011–2014, 2000.

W.G. Overend in "The Carbohydrates", vol. 1A, W. Pigman and D. Horton, eds, Academic Press, New York and London, 1972 p 342, lines 24–32.

Kohata, et al., "Anomeric Configuration Analysis–Extension of the Ring Oxygen Helicity Rule to Aromatic Glycofuranosides", Agric. Biol. Chem., vol. 46, No. 8, p 2077–2086, 1982.

*Primary Examiner*—Samuel Barts
*Assistant Examiner*—Michael C. Henry
(74) *Attorney, Agent, or Firm*—Merchant & Gould P.C.

(57) ABSTRACT

A β-D-glucofuranose compound which is 1,2,3,5,6-penta-O-propanoyl-β-D-glucofuranose, preferably in crystalline form, is prepared from D-glucose. The compound is prepared by reacting D-glucose with boric acid, or an equivalent thereof, followed by treatment with a propanoylating reagent, preferably propanoic anhydride. The compound is useful for the preparation of other compounds, such as glucofuranosides.

7 Claims, No Drawings

GLUCOFURANOSES

This is the National Phase Application of PCT/N200/0028, filed Nov. 16, 2000.

This invention relates to a perpropanoylated glucofuranose, its preparation from glucose, and its use in the preparation of other compounds. In particular, the invention relates to crystalline 1,2,3,5,6-penta-O-propanoyl-β-D-glucofuranose, a process for preparing it, and its use in the preparation of various glycosides and other compounds.

BACKGROUND

A large number of carbohydrate compounds are cheap and readily available starting materials useful in the synthesis of a wide variety of substances. One particularly desirable feature of carbohydrate compounds is that they are a source of one or more chiral carbon atoms. Many compounds useful in the pharmaceutical, agrochemical, and other industries, contain one or more chiral carbon atoms. Such compounds can be prepared in a more effective manner from carbohydrate starting materials than from non-chiral starting materials which therefore require the introduction of chirality during the synthetic route.

Examples of monosaccharide carbohydrates often used as starting materials include glucose, mannose, galactose, ribose, and arabinose. Disaccharides, for example lactose, trisaccharides, and other higher order saccharides, are also useful starting materials for the preparation of desirable compounds.

Most carbohydrate compounds contain several hydroxyl groups. Monosaccharides typically have four or five hydroxyl groups. The selective reaction of one or more of the hydroxyl groups of a monosaccharide is usually required during the synthetic route to a desired product. It is therefore often necessary to protect some or all of the hydroxyl groups of a monosaccharide in the form of ester groups, or other protecting groups.

Protection of one or more of the hydroxyl groups is often the first reaction of a sequence performed on the unprotected monosaccharide starting material.

Most readily available monosaccharide starting materials have a pyranose structure, although in solution the monosaccharide will interconvert between the pyranose form and the furanose form. The pyranose form contains a 6-membered oxygenated ring whereas the furanose form contains a 5-membered oxygenated ring. Both forms may have either an α or β orientation of the hydroxyl group at C-1.

In many instances it is useful to convert the starting material monosaccharide into a protected furanose compound. The cheapest and most readily available monosaccharide starting material is glucose. Glucose can be protected by acetylating each hydroxyl group of glucose to give peracetylated glucopyranose. Peracetylated glucopyranose can be readily prepared in one step from glucose. However, the preparation of the furanose form is less straight forward.

The preparation of peracetylated glucofuranose is known but usually requires several reaction steps and has a low overall yield of product. A common method is to constrain the glucose to the furanose form by formation of diacetone glucose. Partial hydrolysis, acetylation and subsequent acetolysis gives peracetylated glucofuranose. Another method involves the initial preparation of glucose diethyl dithioacetal followed by cyclisation in the presence of mercury salts and then acetylation.

Peracetylated glucofuranose can be also prepared from glucose in one step in the presence of a reagent such as $FeCl_3$ or Montmorillonite clays. However, these one-step methods proceed in low yields and the products are unavoidably contaminated by significant amounts of pyranose products.

It is known to prepare perbenzoylated glucofuranose from glucose, but in several steps. For example, glucose can be treated with boric acid to give a boron complex of the glucose. The complex can be reacted with benzoyl chloride to give dibenzoylated glucose. Successive repetitions of similar procedures lead ultimately to the perbenzoylated glucofuranose.

The known methods of preparing a protected glucofuranose from an unprotected monosaccharide starting material require several reaction steps and are therefore laborious, time consuming and consequently expensive.

Additionally, a problem with many glucofuranose derivatives is that they are oils at normal temperatures and pressures, rather than crystalline solids. This means that it can be very difficult and time consuming to purify the glucofuranose. Often the α- and β- forms of a glucofuranose have very similar physical properties making it difficult to separate one from the other by standard methods, such as chromatography. However, if one or both of the α- and β- forms is crystalline, either may be readily separated from the other by recrystallisation from a suitable solvent.

Furthermore, peracylation of an unprotected saccharide typically gives a mixture of C-1 α and β products. Often only one of the α and β products is desired for further reaction. For example, a C-1 β acetate on a glucose ring can be more reactive than the C-1α counterpart towards displacement by nucleophiles due to the effect of neighbouring group participation. Thus, the comparatively mild conditions needed for the synthesis of furanosides from a C-1 β acetate can minimise any undesired anomerisation during the reaction, leading to a predominance of β-furanoside product over the α-furanoside form. β-Furanosides are of particular synthetic interest because, for example, the nucleotides in RNA contain β-furanoside moieties.

It is therefore an object of this invention to provide a novel peracylated glucofuranose, or to at least provide a useful alternative.

STATEMENTS OF INVENTION

In a first aspect of the invention there is provided a peracylated glucofuranose which is 1,2,3,5,6-penta-O-propanoyl-β-D-glucofuranose, preferably in crystalline form.

In a second aspect of the invention there is provided a process for the preparation of 1,2,3,5,6-penta-O-propanoyl-β-D-glucofuranose from D-glucose. Preferably, the process includes the steps of reacting D-glucose with boric acid, or an equivalent thereof, to give a boron-glucose intermediate and reacting the intermediate with a propanoylating reagent, such as propanoic anhydride.

In a third aspect of the invention there is provided a use of 1,2,3,5,6-penta-O-propanoyl-β-D-glucofuranose in the preparation of another compound, preferably a β-D-glucofuranoside.

DETAILED DESCRIPTION

The term "unprotected saccharide" includes any saccharide which is fully or at least partially unprotected. Such compounds will have at least two free hydroxyl groups including the hydroxyl group at the C-1 position of the reducing-sugar residue. Generally, unprotected saccharides are fully unprotected, for example, each oxygen function at positions C-1, C-2, C-3, C-4 and C-6 of a pyranose monosaccharide will be in the form of hydroxyl groups rather than ethers, esters and the like. Unprotected saccharides may have fewer hydroxyl groups, such as 1–6 disaccharides which have the C-6 oxygen function of the reducing ring linked to a monosaccharide, for example, isomaltose, allolactose and gentiobiose.

The term "peracylated" means that all hydroxyl groups of the corresponding unprotected saccharide have been converted to an ester group. The term "peracetylated" therefore means that each available hydroxyl group of the unprotected saccharide has been converted to an acetate group.

The term "disaccharide" refers to a compound in which two monosaccharides are joined by a glycosidic linkage. The term "oligosaccharide" refers to those saccharides having a well-defined structure comprising a known number (greater than 2) of known monosaccharides joined by glycosidic linkages.

The term "reducing-sugar residue" refers to the residue of a saccharide that has, in its unprotected form, a C-1 hydroxyl group and which is capable of being in an aldehydic form.

The terms α and β relate to the stereochemical arrangement of an atom or group of atoms relative to the plane of the monosaccharide ring structure. Thus, for example, a C-1 α acetate means that the acetate group lies below the plane of the carbohydrate ring whereas a C-1 β acetate means the acetate group lies above the plane of the carbohydrate ring when drawn in the conventional manner.

The compound of the invention is 1,2,3,5,6-penta-O-propanoyl-β-D-glucofuranose. It has been found that the compound can be readily obtained in crystalline form. This means that purification of the compound, for example by recrystallisation, is simplified relative to the purification of non-crystalline products, for example by chromatographic techniques. It is often difficult to separate the C-1 α and β isomers of a particular compound by chromatographic techniques.

The compound 1,2,3,5,6-penta-O-propanoyl-β-D-glucofuranose is obtained by treating D-glucose with boric acid in the presence of propanoic acid. A propanoylating reagent, such as propanoic anhydride, is then added to the reaction mixture. The product is obtained as a crystalline solid.

In a typical reaction of the process of the invention, glucose is treated with 2 or more mole equivalents of boric acid in propanoic acid. The reaction mixture is stirred at approximately 70° C. for approximately one hour. Propanoic anhydride, optionally together with sulfuric acid, is added and the reaction is maintained at approximately 70° C. while stirring for a time sufficient to give 1,2.3,5,6-penta-O-propanoyl-β-D-glucofuranose.

While the process of the invention relates to the use of boric acid, it is intended that any boron reagent may be used which acts in a like manner to boric acid during the process. For example, it is envisaged that certain borate esters and salts may act as functional equivalents of boric acid during the reaction.

It is thought that the boric acid (or an equivalent thereof) complexes with the oxygen atoms at the 1- and 2- positions of the furanose form of glucose thereby stabilising that form relative to the pyranose form. Acylation then proceeds to give a predominance of the 1-β ester. Further, in the case of propanoylation of the glucose, the product is crystalline and can be readily recovered in substantially pure form from the reaction mixture.

The invention is further described with reference to the following examples which are not to be taken as limiting the invention as described.

EXAMPLES

Example 1

1,2,3,5,6-Penta-O-propanoyl-β-D-glucofuranose

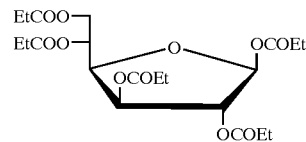

D-Glucose (5.0 g, 27.8 mmol), boric acid (3.5 g, 56.9 mmol, 2.05 eq.) and propanoic acid (75 mL) were stirred at 70° C. for one hour. By this time, all the D-glucose had dissolved. Propanoic anhydride (75 mL) was added slowly and the resulting mixture was heated at 70° C. for 48 hours. The reaction mixture was diluted to 1000 mL with ice (100 g) and water and the mixture stirred vigorously for one hour. The resulting precipitate was collected by filtration and recrystallised twice from ethanol (20 mL) to give the title compound as white prisms (7.4 g, 58%); mp 74.5–75.5° C., $[\alpha]_D^{22}$ –30.8 (c 5.0, CHCl$_3$). IR (CDCl$_3$) 2987, 1740 cm$^{-1}$. $^1$H NMR (CDCl$_3$): δ 6.14 (s, 1H, H1), 5.42 (d, 1H, J=4.8 Hz, H3), 5.29 (ddd, 1H, J=9.4, 5.2, 2.5, Hz, H5), 5.10 (s, 1H, H2), 4.63 (dd, 1H, J=12.3, 2.5 Hz, H6a), 4.55 (dd, 1H, J=9.4, 4.7 Hz, H4), 4.10 (dd, 1H, J=12.3, 5.2 Hz, H6b), 2.40 (q, 2H, J=7.6 Hz), 2.38 (q, 2H, J=7.6 Hz), 2.37 (q, 2H, J=7.6 Hz), 2.34 (q, 2H, J=7.6 Hz), 2.26 (q, 2H, J=7.6 Hz) (5×CH$_2$), 1.17 (t, 6H, J=7.6 Hz), 1.13 (t, 6H, J=7.6 Hz), 1.09 (t, 3H, J=7.6 Hz) (5×CH$_3$) ppm. $^{13}$C NMR (CDCl$_3$): δ 174.3, 173.4, 173.0, 172.9 (2) (5×C=O), 99.2 (C1), 80.2 (C4), 79.9 (C2), 73.2 (C3), 68.6 (C5), 63.3 (C6), 28.0, 27.7 (3), 27.6 (5×CH$_2$), 9.4, 9.2 (2), 9.1 (2) (5×CH$_3$) ppm. LRMS (FAB) 387 (M$^+$-C$_3$H$_5$O$_2$, 100%), 183 (24), 137 (25), 57 (52) m/z. HRMS (FAB): calcd for C$_{21}$H$_{32}$O$_{11}$ (M$^+$-H) 459.186360, found 459.186637. Anal: calcd for C$_{21}$H$_{32}$O$_{11}$: C 54.78; H 7.00. Found: C 54.80; H 6.96.

The perpropanoylated glucofuranose of Example 1 was obtained in crystalline form and in greater than approximately 90% anomeric purity. The compound is therefore desirable is a starting material for the synthesis of other compounds containing chiral carbon atoms.

Example 2

Ethyl α/β-D-glucofuranoside

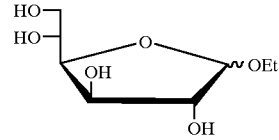

1,2,3,5,6-Penta-O-propanoyl-β-D-glucofuranose (2.0 g, 4.3 mmol) was dissolved in CH$_2$Cl$_2$ (10 mL) and anhydrous EtOH (1.3 mL, 21.7 mmol) was added, followed by the dropwise addition of boron trifluoride diethyl etherate (3.3 mL, 26.0 mmol). After 1 h at room temperature, the solution was washed with saturated aqueous NaHCO$_3$ (2×30 mL), brine, dried (MgSO$_4$) and concentrated in vacuo. Flash silica chromatography of the residue, eluting with 10% ethyl acetate in petroleum ether, gave ethyl 2,3,5,6-tetra-O-propanoyl-α/β-D-glucofuranoside as a colourless syrup (1.1 g, 56%).

This anomeric mixture (830 mg, 1.9 mmol) was dissolved in methanol saturated with ammonia (8 mL) and left at room temperature overnight. After concentrating in vacuo, the resulting residue was purified by flash silica chromatography, eluting with 5% methanol in CHCl$_3$, to give ethyl α/β-D-glucofuranose (374 mg, 94%). The two anomers were almost indistinguishable by TLC (CHCl$_3$/MeOH 10%).

The first few fractions gave ethyl α-D-glucofuranoside as colourless needles, mp 82.5–84° C. (lit.[1] 82–83° C.), $[\alpha]_D^{21}$=+95.8 (c 0.8 in H$_2$O) [lit.[1] $[\alpha]_D$=+98 (H$_2$O)]; $\delta_H$ (D$_2$O) 5.18 (1H, d, J4.2, 1-H), 4.27 (1H, dd, J 4.2 and 3.6, 3-H), 4.12 (1H, dd, J 4.2 and 3.6, 2-H), 4.08 (1H, dd, J 7.9 and 4.2, 4-H), 3.85 (1H, ddd, J 7.9, 6.3 and 2.8, 5-H), 3.79 (1H, qd, J 7.2 and 9.3, CHCH$_3$), 3.77 (1H, dd, J 12.0 and 2.8, 6a-H), 3.62 (1H, dd, J 12.0 and 6.3, 6b-H), 3.60 (1H, qd, J 7.2 and 9.3, CHCH$_3$), 1.18 (3H, t, J 7.2, CH$_3$); $\delta_C$ (D$_2$O) 102.4 (1-C), 78.2 (4-C), 75.0 (2-C), 76.1 (3-C), 70.1 (5-C), 65.6 (CH$_2$), 63.6 (6-C), 14.7 (CH$_3$).

The last few fractions gave ethyl β-D-glucofuranoside as a colourless oil, (lit.[1] mp 59–60° C.), [lit.[1] $[\alpha]_D$=−86 (H$_2$O)]; $\delta_H$(D$_2$O) 4.94 (1H, s, 1-H), 4.19 (1H, d, J 4.4, 3-H), 4.11 (1H, dd, J 8.9 and 4.4, 4-H), 4.08 (1H, s, 2-H1), 3.93 (1H, ddd, J 8.9, 6.0 and 2.6, 5-H), 3.80 (1H, dd, J 12.0 and 2.6, 6a-H), 3.71 (1H, qdd, J 7.1, 10.0 and 0.6, CHCH$_3$), 3.64. (1H, dd, J 12.0 and 6.0, 6b-H), 3.53 (1H, qdd, J 7.1, 10.0 and 0.6, CHCH$_3$), 1.15 (3H, td, J 7.1 and 0.6, CH$_3$); $\delta_C$ (D$_2$O) 108.3 (1-C), 81.4 (4-C), 80.2 (2-C), 75.3 (3-C), 70.1 (5-C), 64.8 (CH$_2$), 63.9 (6-C), 14.6 (CH$_3$).

Example 3

Phenyl β-D-glucofuranoside

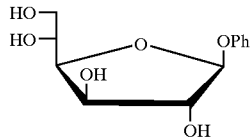

1,2,3,5,6-Penta-O-propanoyl-β-D-glucofuranose (1.0 g, 2.2 mmol) and phenol (0.41 g, 4.3 mmol) were dissolved in CH$_2$Cl$_2$ (10 mL) and boron trifluoride diethyl etherate (134 μL, 1.1 mmol) was added dropwise. The solution was left at room temperature overnight by which time the reaction was complete by TLC. The reaction mixture was washed with saturated aqueous NaHCO$_3$ (30 mL), water, dried (MgSO$_4$) and concentrated in vacuo. Flash silica chromatography of the residue, eluting with 15% ethyl acetate in petroleum ether, gave phenyl 2,3,5,6-tetra-O-propanoyl-β-D-glucofuranoside as a colourless syrup (0.8 g, 77%); $\delta_H$ (CDCl$_3$) 7.29 (2H, dd, J 7.4 and 8.4, 3'-and 5'-H), 7.02 (1H, t, J 7.4, 4'-H), 7.01 (2H, d, J 8.4, 2'- and 6'-H), 5.63 (1H, s, 1-H), 5.46 (1H, d, J 5.0, 3-H), 5.31 (1H, ddd, J 9.4, 4.6 and 2.4, 5-H), 5.27 (1H, s, 2-H), 4.62 (1H, dd, J 9.4 and 5.0, 4-H), 4.54 (1H, dd, J 12.3 and 2.4, 6a-H), 4.09 (1H, dd, J 12.3 and 4.6, 6b-H), 2.42 (2H, q, J 7.5, CH$_2$), 2.39 (2H, q, J 7.5, CH$_2$), 2.33 (2H, q, J 7.5, CH$_2$), 2.25 (2H, q, J 7.5, CH$_2$), 1.17 (3H, t, J 7.5, CH$_3$), 1.15 (3H, t, J 7.5, CH$_3$), 1.13 (3H, t, J 7.5, CH$_3$), 1.08 (3H, t, J 7.5, CH$_3$); $\delta_C$ (CDCl$_3$) 174.3, 173.3, 173.3, 173.0 (4×C=O), 156.6 (1'-C), 130.0 (3'- and 5'-C), 122.9 (4'-C), 116.9 (2'- and 6'-C), 104.6 (1-C), 80.7 (2-C), 79.7 (4-C), 73.6 (3-C), 68.9 (5-C), 63.2 (6-C), 27.8, 27.8, 27.8, 27.7 (4×CH$_2$), 9.4, 9.2, 9.2, 9.1 (4×CH$_3$).

Phenyl 2,3,5,6-tetra-O-propanoyl-β-D-glucofuranoside was dissolved in methanol (10 mL) and 1 M sodium methoxide in methanol was added until the pH=12. The solution was left for 2 hours and then neutralised with Amberlite IRC-50 (H) resin, filtered and concentrated in vacuo. The resulting residue was purified by flash silica chromatography, eluting with 10% methanol in CHCl$_3$, to give the product as a colourless oil (390 mg). This was crystallised from butan-2-one/petroleum ether to give phenyl β-D-glucofuranoside (220 mg, 52%) which was identical to that prepared earlier.[2]

Example 4

4-Nitrophenyl (α/β-D-glucofuranoside

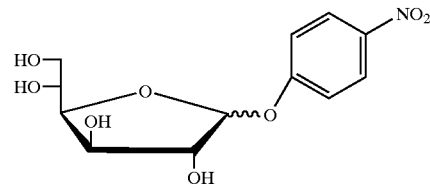

1,2,3,5,6-Penta-O-propanoyl-β-D-glucofuranose (1.0 g, 2.2 mmol) and 4-nitrophenol (604 mg, 4.3 mmol) were dissolved in CH$_2$Cl$_2$ (10 mL) and boron trifluoride diethyl etherate (134 μL, 1.1 mmol) was added dropwise. The solution was left overnight and was then washed with saturated aqueous NaHCO$_3$ (30 mL), water, dried (MgSO$_4$) and concentrated in vacuo. Flash silica chromatography of the residue, eluting with 20% ethyl acetate in petroleum ether, gave a colourless syrup containing an anomeric mixture of the 4-nitrophenyl 2,3,5,6-tetra-O-propanoyl-β-D-glucofuranosides (0.99 g).

This anomeric mixture was dissolved in methanol (20 mL) and aq. NaOH (1 M) was added until the solution pH=10. The solution was left overnight and then neutralised with Amberlite IRC-50 (H) resin, filtered and concentrated in vacuo. The resulting residue was purified by flash silica chromatography, eluting with 10% methanol in CHCl$_3$, to give 4-nitrophenyl α/β-D-glucofuranoside as a pale yellow oil (400 mg, 61% overall, α:β=2:9). Further careful chromatography allowed separation of the anomers.

4-Nitrophenyl α-D-glucofuranoside was recrystallised from butan-2-one to give colourless needles, mp 117.5–119.5° C. (from butan-2-one), $[\alpha]_D^{24}$=+211.5 (c 1.0 in H$_2$O); $\delta_H$ (d$_6$-DMSO) 8.22 (2H, d, J 9.2, 3'- and 5'-H), 7.17 (2H, d, J 9.2, 2'- and 6'-H), 5.59 (1H, d, J 4.2, 1-H), 5.41 (1H, s, HO), 5.05 (1H, s, HO), 4.66 (1H, s, HO), 4.41 (1H, s, HO), 4.28 (1H, dd, J 4.3 and 4.2, 2-H), 4.14 (1H, dd, J 4.3 and 2.7, 3-H), 3.98 (1H, dd, J 8.4 and 2.7, 4-H), 3.79 (1H, ddd, J 8.4, 5.9 and 2.8, 5-H), 3.55 (1H, dd, J 11.2 and 2.8, 6a-H), 3.34 (1H, dd, J 11.2 and 5.9, 6b-H); $\delta_C$ (d$_6$-DMSO) 162.7 (1'-C), 141.9 (4'-C), 126.2 (3'- and 5'-C), 116.9 (2- and 6'-C), 106.7 (1-C), 81.6 (4-C), 77.7 (2-C), 71.0 (3-C), 69.3 (5-C), 63.4 (6-C).

4-Nitrophenyl β-D-glucofuranoside was isolated as a pale yellow oil, $[\alpha]_D^{20}$=114.6 (c 3.2 in H$_2$O); $\delta_H$ (d$_6$DMSO) 8.13 (2H, d, J 9.3, 3'- and 5'-H), 7.09 (2H, d, J 9.3, 2'- and 6'-H), 5.66 (1H, s, HO), 5.55 (1H, s, 1-H), 5.06 (1H, s, HO), 4.59 (1H, s, HO), 4.38 (1H, s, HO), 4.21 (1H, s, 2-H), 4.13–4.09 (2H, m, 3- and 4-H), 3.72 (1H, ddd, J 8.1, 6.0 and 2.8, 5-H), 3.51 (1H, dd, J 11.6 and 2.8, 6a-H), 3.34 (1H, dd, J 11.6 and 6.0, 6b-H); $\delta_C$ (d$_6$-DMSO) 161.7 (1'-C), 141.7 (4'-C), 126.0 (3'- and 5'-C), 116.6 (2'- and 6'-C), 105.9 (1-C), 83.0 (4-C), 80.5 (2-C), 74.6 (3-C), 69.3 (5-C), 63.4 (6-C).

Example 5

Methyl 2,3,5,6-tetra-O-propanoyl-1-thio-β-D-glucofuranoside

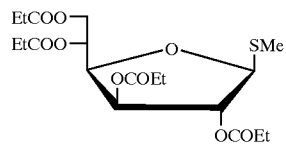

1,2,3,5,6-Penta-O-propanoyl-β-D-glucofuranose (614 mg, 1.3 mmol) was dissolved in 1,2-dichloroethane (5 mL) and cooled to 0° C. (Methylthio)trimethylsilane (567 µL, 4.0 mmol) was added dropwise followed by trimethylsilyl trifluoromethanesulfonate (72 µL, 0.4 mmol). After 20 min at room temperature, the mixture was heated at 50° C. for 3 h, cooled, diluted with CHCl$_3$, washed with 50% aqueous NaHCO$_3$ (30 mL), brine, dried (MgSO$_4$) and concentrated in vacuo. Flash silica chromatography of the residue, eluting with 10% ethyl acetate in petroleum ether, gave methyl 2,3,5,6-tetra-O-propanoyl-1-thio-β-D-glucofuranoside as a colourless solid (470 mg, 81%). A sample was recrystallised from ethanol to give colourless needles, mp 62–63° C. (from EtOH), $[\alpha]_D^{22}$=−50.5 (c 1.0 in CHCl$_3$), (Found: C, 52.7; H, 7.2; S, 7.4. C$_{19}$H$_{30}$O$_9$S requires C, 52.5; H, 7.0; S 7.4%); $\delta_H$ (CDCl$_3$) 5.37 (1H, d, J 4.2, 3-H), 5.33 (1H, ddd, J 9.3, 5.1 and 2.5, 5-H), 5.07 (1H, d, J 2.2, 2-H), 5.00 (1H, d, J 2.2, 1-H), 4.62 (1H, dd, J 12.3 and 5.1, 2.5, 6a-H), 4.36 (1H, dd, J 9.3 and 4.2, 4-H), 4.17 (1H, dd, J 12.3 and 5.1, 6b-H), 2.39 (2H, q, J 7.6, CH$_2$), 2.37 (2H, q, J 7.6, CH$_2$), 2.35 (2H, q, J 7.6, CH$_2$), 2.26 (2H, q, J 7.6, CH$_2$), 2.23 (3H, s, SCH$_3$) 1.16 (3H, t, J 7.6, CH$_3$), 1.14 (3H, t, J 7.6, CH$_3$), 1.13 (3H, t, J 7.6, CH$_3$), 1.09 (3H, t, J 7.6, CH$_3$); $\delta_C$ (CDCl$_3$) 174.4, 173.3, 173.1, 173.1 (4×C=O), 89.6 (1-C), 81.6 (2-C), 79.1 (4-C), 74.7 (3-C), 68.4 (5-C), 63.4 (6-C), 27.7 (4×CH$_2$), 9.4, 9.2, 9.2, 9.1 (4×CH$_3$); m/z (FAB) 435.169691 (MH$^+$, C$_{19}$H$_{31}$O$_9$S requires 435.168880).

Example 6

Phenyl 1-thio-β-D-glucofuranoside

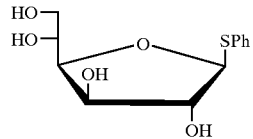

1,2,3,5,6-Penta-O-propanoyl-β-D-glucofuranose (2.0 g, 4.3 mmol) was cooled in an ice/salt bath and thiophenol (670 µL, 6.5 mmol) was added followed by the dropwise addition of boron trifluoride diethyl etherate (640 µL, 5.2 mmol). The solution was allowed to warm to room temperature and was complete after 1 hr by TLC. The reaction mixture was washed with saturated aqueous NaHCO$_3$ (10 mL), water, dried (MgSO$_4$) and concentrated in vacuo. Flash silica chromatography of the residue, eluting with 10% ethyl acetate in petroleum ether, gave phenyl 1-thio-2,3,5,6-tetra-O-propanoyl-β-D-glucofuranoside as a colourless oil (α:β= 1:8).

This anomeric mixture was dissolved in methanol (10 mL) and potassium carbonate (520 mg) was added. After stirring for one hour, the mixture was neutralised with Amberlite IRC-50 (H) resin, filtered and concentrated in vacuo. The resulting residue was recrystallised from ethyl acetate to give phenyl 1-thio-β-D-glucofuranoside as colourless needles (567 mg, 48% overall), mp 105–107° C. (from ethyl acetate) (lit.$^3$ 100° C.), $[\alpha]_D^{23}$=−219.6 (c 1.0 in EtOH), (lit.$^3$ $[\alpha]_D^{21}$=−233 (c 3.0 in EtOH)); $\delta_H$ (d$_6$-DMSO) 7.41 (2H, dd, J 7.2 and 1.3, 2'- and 6'-H), 7.33 (2H, dd, J 7.7 and 7.2, 3'- and 5'-H), 7.22 (1H, tt, J 7.7 and 1.3, 4'-H), 5.63 (1H, s, HO), 5.13 (1H, d. J 1.7, 1-H), 5.09 (1H, s, HO), 4.59 (1H, d, J 4.8, HO), 4.40 (1H, t, J 5.6, HO), 4.05 (1H, s, 2-H), 3.99 (1H, s, 3-H), 3.91 (1H, dd, J 8.2 and 3.5, 4-H), 3.81 (1H, m, 5-H), 3.60 (1H, ddd, J 11.3, 5.6 and 3.1, 6a-H), 3.40 (1H, ddd, J 11.3, 5.7 and 5,6, 6b-H). $\delta_C$ (d$_6$-DMSO) 137.4 (1'-C), 129.4, 129.3 (2'-, 3'-, 5'- and 6'-C), 126.5 (4'-C), 92.6 (1-C), 82.9 (2- and 4-C), 75.5 (3-C), 69.7 (5-C), 64.0 (6-C); m/z (FAB) 272.070870 (M$^+$, C$_{12}$H$_{16}$O$_5$S requires 272.071846).

Example 7

1-β-D-Glucofuranosyluracil

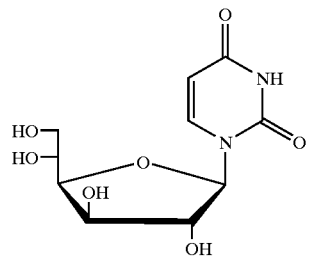

To a suspension of 1,2,3,5,6-penta-O-propanoyl-β-D-glucofuranose (2.0 g, 4.3 mmol) and uracil (730 mg, 6.5 mmol) in CH$_3$CN (30 mL) was added N,O-bis (trimethylsilyl)acetamide (6.4 mL, 26.1 mmol) dropwise. The mixture was heated at 60° C. for 1 h by which time the suspension had dissolved. The mixture was cooled to 0° C. and trimethylsilyl trifluoromethanesulfonate (1.6 mL, 8.7 mmol) was added dropwise. After 5 h reflux, the solution was concentrated in vacuo to half the volume and cooled in an ice-bath. Saturated aqueous NaHCO$_3$ (60 mL) was added and the mixture extracted with CH$_2$Cl$_2$ (60, 2×30 mL). The combined extracts were washed with brine, dried (MgSO$_4$) and concentrated in vacuo. Flash silica chromatography of the residue, eluting with 1% CH$_3$OH in CHCl$_3$, gave 1-(2, 3,5,6-tetra-O-propanoyl-β-D-glucofuranosyl)uracil as a colourless syrup (2.1 g, 96%), $[\alpha]_D^{22}$=+14.6 (c 1.0 in CHCl$_3$), (Found: C. 52.7; H, 6.1; N, 5.7. C$_{22}$H$_{30}$N$_2$O$_{11}$ requires C, 53.0; H, 6.1; N 5.6%); $\delta_H$ (CDCl$_3$) 9.34 (1H, s, NH), 7.47 (1H, d, J 8.2, 6-H), 6.06 (1H, d, J 2.0, 1'-H), 5.82 (1H, d, J 8.2, 5-H), 5.45 l1H, d, J 3.3, 3'-H), 5.36 (1H, ddd, J 9.6, 5.4 and 2.4, 5'-H), 5.07 (1H, d, J 2.0, 2'-H), 4.61 (1H, dd, J 12.3 and 2.4, 6'a-H), 4.38 (1H, dd, J 9.6 and 3.3, 4'-H), 4.11 (1H, dd, J 12.3 and 5.4, 6'b-H), 2.45 (2H, qd, J 7.5 and 1.5, CH$_2$), 2.36 (2H, q, J 7.5, CH$_2$), 2.35 (2H, q, J 7.5, CH$_2$), 2.29 (2H, q, J 7.5, CH$_2$), 1.18 (3H, t, J 7.5, CH$_3$), 1.15 (3H, t, J 7.5, CH$_3$), 1.12 (3H, t, J 7.5, CH$_3$), 1.10 (3H, t, J 7.5, CH$_3$); $\delta_C$ (CDCl$_3$) 174.3, 173.4, 172.8, 172.3 (4×C=O), 163.2 (3-C), 150.4 (2-C), 139.4 (6-C), 103.5 (5-C), 89.7 (1'-C), 80.6 (2'-C), 79.3 (4'-C), 73.5 (3'-C), 67.1 (5'-C), 63.2 (6'-C), 27.7, 27.6, 27.6, 27.5 (4×CH$_2$), 9.4, 9.1, 9.1, 9.0 (4×CH$_3$); m/z (FAB) 499.191398 (MH$^+$, C$_{22}$H$_{31}$N$_2$O$_{11}$ requires 499.192785).

1-(2,3,5,6-Tetra-O-propanoyl-β-D-glucofuranosyl)uracil was dissolved in methanol saturated with ammonia (15 mL) and left at room temperature overnight. After concentrating in vacuo, the resulting residue was purified by flash silica chromatography, eluting with CHCl$_3$/CH$_3$OH/NH$_3$ aq. (84:15:1), to give 1-βD-glucofuranosyluracil as a colourless solid (680 mg, 75%). A sample was recrystallised from EtOH to give the product as colourless needles, mp 175–176.5° C. (from EtOH), $[\alpha]_D^{21}$=+9.91 (c 1.1 in H$_2$O), (Found: C, 44.0; H, 5.0; N, 10.35. C$_{10}$H$_{14}$N2O$_7$ requires C, 43.8; H, 5.15; N, 10.2%); $\delta_H$ (D$_2$O) 7.82 (1H, d, J 8.1, 6-H), 5.79 (1H, d, J 8.1, 5-H), 5.75 (1H, s, 1'-H), 4.27–4.25 (2H, m, 2'- and 3'-H), 4.23 (1H, dd, J 8.6 and 2.7, 4'-H), 4.12 (1H, ddd, J 8.6, 5.4 and 2.7, 5'-H), 3.86 (1H, dd, J 12.1 and 2.7, 6'a-H), 3.37 (1H, dd, J 12.1 and 5.4, 6'b-H); $\delta_C$ (D$_2$O) 166.8 (3-C), 151.9 (2-C), 142.6 (6-C), 101.5 (5-C), 92.4 (1'-C), 82.8 (4'-C), 80.7, 74.7 (2'- and 3'-C), 68.9 (5'-C), 63.8 (6'-C); m/z (FAB) 275.088448 (MH$^+$, C$_{10}$H$_{15}$N$_2$O$_7$ requires 275.087926).

Where in the foregoing description reference has been made to terms or expressions having known equivalents, such equivalents are incorporated as if individually set forth.

Although this invention has been described by way of example, it is to be appreciated that improvements and/or modifications may be made thereto without departing from the scope of the claims.

REFERENCES

1. *Dictionary of Organic Compounds*; 5th ed.; Chapman & Hall: New York, 1982; Vol. 3.
2. Furneaux, R. H.; Rendle, P. M.; Sims, I. M.; *J. Chem. Soc., Perkin Trans.* 1, 2000, 2011–2014.
3. K. Kohata, H. Meguro, *Agric. Biol. Chem.*, 46 (1982) 2077–2086.

What is claimed is:

1. A compound which is 1,2,3,5,6-penta-O-propanoyl-β-D-glucofuranose.

2. The compound as claimed in claim 1 in crystalline form.

3. A process for the preparation of 1,2,3,5,6-penta-O-propanoyl-β-D-glucofuranose including:

reacting D-glucose with a boron reagent to give a glucose-boron intermediate, and reacting the glucose-boron intermediate with a propanoylating reagent.

4. The process as claimed in claim 3 where the boron reagent is boric acid.

5. The process as claimed in claim 3 where the propanoylating reagent is propanoic anhydride.

6. The process as claimed in claim 3 where the 1,2,3,5,6-penta-O-propanoyl-β-D-glucofuranose is prepared in crystalline form.

7. The process as claimed in claim 6 where the 1,2,3,5,6-penta-O-propanoyl-β-D-glucofuranose is purified by recrystallisation from ethanol.

* * * * *